US011759156B2

(12) United States Patent
Jenkins et al.

(10) Patent No.: US 11,759,156 B2
(45) Date of Patent: *Sep. 19, 2023

(54) INDEPENDENTLY ROTATABLE DETECTOR PLATE FOR MEDICAL IMAGING DEVICE (71) Applicant: Hologic, Inc., Marlborough, MA (US)

(72) Inventors: John Jenkins, Tyngsboro, MA (US); Mark Guetersloh, Bedford, MA (US); Aleksey Danilkin, Maynard, MA (US); Tri Pham, Arlington, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/704,403

(22) Filed: Mar. 25, 2022

(65) Prior Publication Data

US 2022/0249044 A1 Aug. 11, 2022

Related U.S. Application Data (63) Continuation of application No. 17/002,329, filed on Aug. 25, 2020, now Pat. No. 11,311,258, which is a
(Continued)

(51) Int. Cl.
*A61B 6/00* (2006.01)
*G21K 1/04* (2006.01)
*A61B 6/06* (2006.01)

(52) U.S. Cl.
CPC .............. *A61B 6/4441* (2013.01); *A61B 6/06* (2013.01); *A61B 6/4452* (2013.01); *A61B 6/461* (2013.01);
(Continued)

(58) Field of Classification Search
CPC ....... A61B 6/06; A61B 6/4441; A61B 6/4452; A61B 6/461; A61B 6/487; A61B 6/4233; A61B 6/4405; A61B 6/025; A61B 6/505; A61B 6/0487; A61B 6/4241; A61B 6/547; A61B 6/022; A61B 6/4258; A61B 6/12; A61B 6/107; A61B 6/5235; A61B 6/0407;
(Continued)

(56) References Cited

U.S. PATENT DOCUMENTS 2,881,329 A   4/1959   Peyser
4,991,189 A   2/1991   Boomgaarden
(Continued)

FOREIGN PATENT DOCUMENTS

WO   2012/173597   12/2012

*Primary Examiner* — Irakli Kiknadze
(74) *Attorney, Agent, or Firm* — Merchant & Gould P.C.

(57) ABSTRACT

A real-time fluoroscopic imaging system includes a collimator and a detector which are rotationally movable independent of the support assembly, e.g., c-arm, to which they are mounted. Rotational movement of the collimator and the detector are coordinated such that the orientation of the detector with respect to the collimator does not change. The collimator may include a geared flange member to facilitate rotation, and may be a single molded piece formed of a plastic such as tungsten polymer material. The system may also include a plurality of interchangeable collimators characterized by different shapes. A display is provided to present an image to an operator, and image orientation logic displays a target anatomy in a selected orientation regardless of orientation of the target anatomy relative to the detector, and regardless of rotation of the detector.

23 Claims, 10 Drawing Sheets

Related U.S. Application Data continuation of application No. 16/355,697, filed on Mar. 15, 2019, now Pat. No. 10,786,216, which is a continuation of application No. 15/861,863, filed on Jan. 4, 2018, now Pat. No. 10,271,807, which is a continuation of application No. 14/884,934, filed on Oct. 16, 2015, now Pat. No. 9,872,659, which is a continuation of application No. 13/223,866, filed on Sep. 1, 2011, now Pat. No. 9,161,727.

(52) U.S. Cl.
CPC ............... *A61B 6/487* (2013.01); *G21K 1/04* (2013.01); *A61B 6/4233* (2013.01)

(58) Field of Classification Search
CPC ..... A61B 6/0421; A61B 6/588; A61B 6/4464; A61B 6/545; A61B 6/4482; A61B 6/587; A61B 6/585; A61B 6/08; A61B 6/54; A61B 6/582; A61B 6/4476; A61B 6/032; A61B 6/4429; A61B 6/548; A61B 6/542; A61B 6/4417; A61B 6/584; G21K 1/04; G21K 1/02; A61C 5/50; A61C 5/44; A61C 17/20; A61C 5/40; A61N 5/1042; A61N 5/1082; A61N 5/1048; A61N 5/1081; A61N 5/1045; A61N 5/103; A61N 5/1077; G01T 7/005; G01N 23/046; G01N 2223/303; H04N 5/32
USPC ................................ 378/146–153, 98.2, 205
See application file for complete search history.

(56) References Cited

U.S. PATENT DOCUMENTS

| | | |
|---|---|---|
| 6,215,853 B1 | 4/2001 | Kump |
| 6,370,218 B1 | 4/2002 | Toth |
| 6,974,952 B2 | 12/2005 | Morooka |
| 7,274,774 B2 | 9/2007 | Bates |
| 7,581,884 B1 | 9/2009 | Barnes |
| 7,945,016 B2 | 5/2011 | Bothorel |
| 8,431,909 B2 | 4/2013 | Horton |
| 8,827,554 B2 | 9/2014 | Lalena |
| 9,161,727 B2 | 10/2015 | Jenkins |
| 9,872,659 B2 | 1/2018 | Jenkins |
| 10,271,807 B2 | 4/2019 | Jenkins |
| 10,786,216 B2 | 9/2020 | Jenkins |
| 11,311,258 B2 | 4/2022 | Jenkins |
| 2004/0174953 A1 | 9/2004 | Ikeda |
| 2005/0047552 A1 | 3/2005 | Arai |
| 2009/0238325 A1 | 9/2009 | Kargar |
| 2011/0013742 A1 | 1/2011 | Zaiki |
| 2011/0064193 A1 | 3/2011 | Minnigh |
| 2013/0058462 A1 | 3/2013 | Jenkins |
| 2014/0126694 A1 | 5/2014 | Abenaim |
| 2016/0120490 A1 | 5/2016 | Jenkins |
| 2018/0206806 A1 | 7/2018 | Jenkins |
| 2020/0015765 A1 | 1/2020 | Jenkins |
| 2020/0405249 A1 | 12/2020 | Jenkins |

INDEPENDENTLY ROTATABLE DETECTOR PLATE FOR MEDICAL IMAGING DEVICE

CROSS-REFERENCE TO RELATED APPLICATIONS

This application is a continuation of U.S. patent application Ser. No. 17/002,329 (now U.S. Pat. No. 11,311,258 issued on Apr. 26, 2022), filed on Aug. 25, 2020, which is a continuation of U.S. patent application Ser. No. 16/355,697 filed on Mar. 15, 2019 (now U.S. Pat. No. 10,786,216 issued on Sep. 29, 2020), which is a continuation of U.S. patent application Ser. No. 15/861,863 filed on Jan, 4, 2018 (now U.S. Pat. No. 10,271,807 issued on Apr. 30, 2019), which is a continuation of U.S. patent application Ser. No. 14/884, 934 filed on Oct. 16, 2015 (now U.S. Pat. No. 9,872,659 issued on Jan. 23, 2018), which is a continuation of U.S. patent application Ser. No. 13/223,866 filed Sep. 1, 2011 (now U.S. Pat. No. 9,161,727 issued on Oct. 20, 2015). The above applications are hereby incorporated by reference in their entireties.

FIELD OF THE INVENTION

This invention relates generally to medical imaging, and more particularly to detector plates for medical imaging device.

BACKGROUND OF THE INVENTION

Real-time fluoroscopic imaging systems in which an x-ray emitter is in a fixed relationship relative to an x-ray detector are in widespread use. The emitter and detector are typically mounted on opposing ends of a one-piece support assembly such as a C-shared arm. A variation known as a mini-C-arm is particularly useful for imaging extremities. Various improvements have been made since such imaging systems were initially developed. For example, the x-ray detector may include a digital x-ray flat-panel detector (FPO) with a complementary metal-oxide-semiconductor ("CMOS") device. FPDs have better dynamic range and detection quantum efficiency (DQE) than previous detectors.

It is recognized that it is desirable to reposition the support assembly to which the emitter and detector are mounted. For example, it may be desirable to obtain a second, orthogonal view through the target when repairing a fracture or for implant placement. This can be accomplished by either repositioning the support assembly or, alternatively, using two imaging systems at right angles to one another. The support assembly may be supported by a mechanism that enables rotation about an axis in order to help orient the emitter and detector relative to the target The mechanism may be coupled to a cart or ceiling mount. Regardless of the type of assembly used to fix the position of the emitter relative to the detector, maintaining the relative positioning of the emitter relative to the detector while enabling repositioning of the assembly facilitates ease of use.

SUMMARY OF THE INVENTION

The presently claimed invention is predicated in part on recognition that it may be desirable to re-orient a detector plate that produces a non-circular image. Previous amplifiers and detector plates might be moved rotationally with the c-arm or other support assembly, but were not equipped or required to move rotationally independent of the support assembly because they were circular and produced a circular image, FPDs are typically rectangular in shape and produce a rectangular image. Further, the range of motion of a support assembly such as a c-an is limited. Consequently, it may be desirable to be able to rotate the detector plate and amplifier independent of the support assembly.

In accordance with one non-limiting aspect of the invention an apparatus comprises: an imaging device including an emitter, a collimator, a detector, and a support assembly, the collimator and detector being mounted on the support assembly and being rotationally movable independent of the support assembly.

In accordance with another non-limiting aspect of the invention a method comprises: rotating a detector and a collimator of an imaging device including an emitter and a support assembly, the collimator and detector being mounted on the support assembly and being rotationally moved independent of the support assembly; and providing an image of target anatomy.

DETAILED DESCRIPTION

Figure 1:
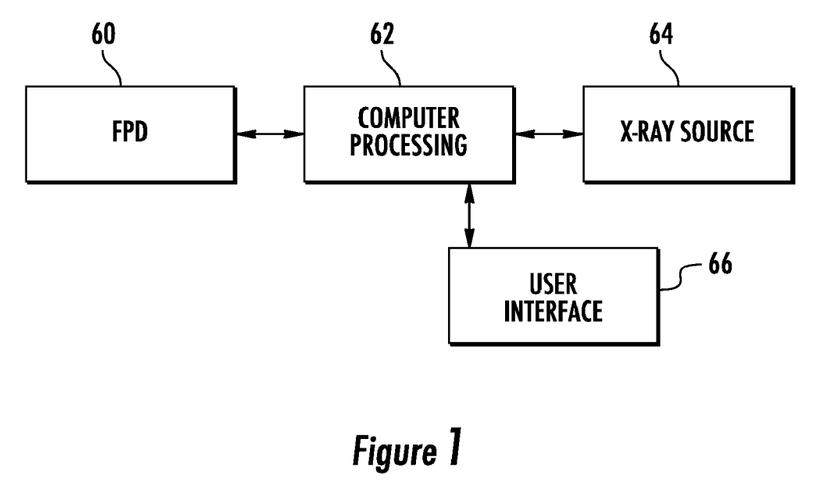
FIG. 1 is a block diagram of the fluoroscopic imaging system.

FIG. 1 is a block diagram of a fluoroscopic imaging system. The system includes a FPD 60, computer processing unit 62, user interface 66, and an x-ray source 64. The x-ray source and FPD operate to generate x-ray images of a selected region of a patient's body. The computer processing unit 62 includes processing hardware and non-transitory computer readable memory for controlling x-ray source 64 and processing x-ray images obtained thereby under corresponding programming. Unit 62 communicates interactively with a user interface 66. The actual physical arrangement of system components may differ from the functional illustration.

Figure 2:
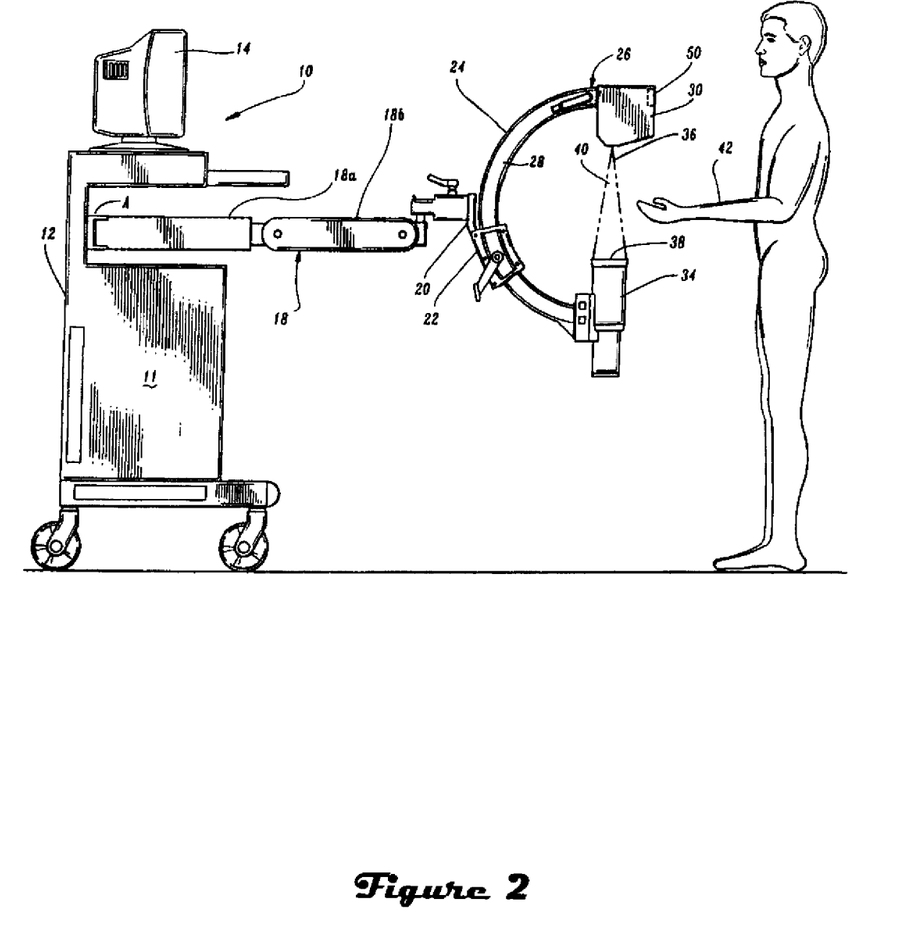
FIG. 2 illustrates an embodiment of the fluoroscopic imaging system.

Referring now to FIG. 2, the imaging system includes an x-ray source assembly 30 and an image detector assembly 34, which can include a flat panel detector (FPD). The x-ray source assembly and image detector assembly are mounted on a mini C-arm assembly 24. The mini C-arm assembly may be mounted to a mobile base 11 via an articulated an assembly 18 for supporting the mini C-Arm in a selected position. The computer processing and a user interface (e.g., keyboard, monitor etc.) may also be mounted on the mobile base. The articulating arm assembly 18 includes two arms 18a and 18b. The distal end of arm 18b is connected to a support arm assembly 20. The C-arm 24 is carried by the support arm assembly 20 such that a track 28 of the C-arm is slidable within the C-arm locking mechanism. The x-ray source assembly 30 and x-ray detector assembly 34 are respectively mounted at opposite extremities of the C-arm in facing relation to each other so that an x-ray beam 36 from x-ray source assembly 30 impinges on the input end 38 of the detector assembly 34. The x-ray source assembly 30 and detector end 38 are spaced apart by the C~arm sufficiently to define a gap 40 between them, in which the limb or extremity of a human patient 42 can be inserted in the path of the x-ray beam 36. The support arm assembly 20 connected to the end of arm 18*b* provides 3-way pivotal mounting that enables the C-arm 24 to be swiveled or rotated through 360° in each of three mutually perpendicular (x, y, z) planes and to be held stably at any desired position, while the arm 18*a* of the articulating arm assembly 18 is mounted to the portable cabinet 11 at point "A" and jointed to enable its distal end and the C-arm to be angularly displaced both horizontally and vertically. The multidirectional angular movability of the C-arm assembly facilitates the positioning of the x-ray source and detector assemblies in relation to a patient body portion to be irradiated.

Figure 3:
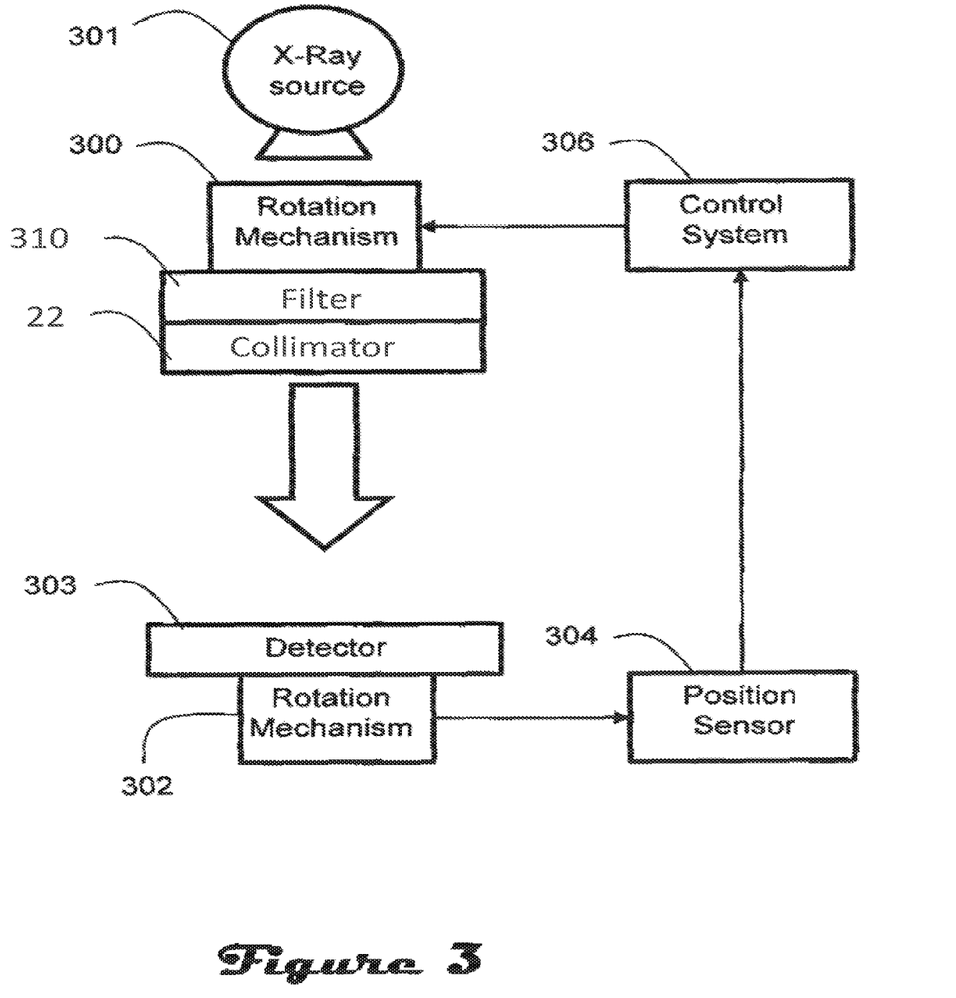
FIG. 3 is a block diagram of the scanner.

Referring to FIGS. 2 and 3, the source assembly 30 includes an X-ray source 301, rotation mechanism 300, and collimator 22. Furthermore, the detector assembly 34 includes a detector 303 and rotation mechanism 302. X-rays emitted by the x-ray source 301 are limited by the collimator 22 into a distribution characterized by a selected shape. An x-ray filter 310 is placed in the x-ray beam to eliminate variations in x-ray dose that are inherent in the x-ray tube output. The collimated x-rays are projected onto the image detector 303. An anatomical target, e.g., a hand or foot, is disposed between the source and the detector for imaging. The x-rays which pass through the target impinge on the x-ray detector, which produces raw x-ray data that is provided to the computer processing unit. The computer processing unit produces a set of pixel values for a projection image from the raw x-ray energy measurements. The pixel values are used to display an image on the interface.

The collimator 22 and detector 303 are rotationally movable independent of the c-arm. In other words, the collimator and detector can each be rotated around an axis without moving the c-am1, which may include rotation of all or part of the source assembly 30 and detector assembly 34. In one embodiment rotational movement of the collimator is enabled by coupling the collimator to the c-arm support assembly via rotation mechanism 300, and rotational movement of the detector is enabled by coupling the detector to the c-arm support assembly via rotation mechanism 302. Previous amplifiers and detector plates were not equipped or required to move rotationally independent of the support assembly because they were circular and produced a circular image. FPDs associated with the detector are typically rectangular in shape and produce a rectangular image. Consequently, there is an advantage to the collimator and detector being rotationally movable independent of the c-arm.

The rotational movement of the collimator, detector, and associated rotation mechanisms are coordinated such that the orientation of the detector with respect to the collimator does not change. For example, the rotation mechanism 300 associated with the collimator may be configured to match the rotation of the mechanism 302 associated with the detector such that manual movement of the detector by the operator is automatically mirrored by the collimator. Alternatively, or additionally, the rotation mechanism associated with the detector may be configured to match the rotation of the mechanism associated with the collimator such that movement of the collimator by the operator is automatically mirrored by the detector. This may be accomplished with a mechanical linkage, an electrical linkage, or any other suitable mechanism. In the illustrated embodiment the rotation mechanism. 302 associated with the detector is coupled to a position sensor 304. As the detector 303 is rotated, the position sensor 304 detects the rotation via the rotation mechanism 302, and provides an indication of the detected rotation to a control system 306. For example, the position sensor may provide an indication of the rotational position of the detector relative to a reference position, or alternatively an indication of change of position in terms such as rotational velocity (rotational speed and direction). The control system 306 operates to produce a corresponding output which prompts the rotation mechanism 300 associated with the collimator to rotate the collimator such that rotation of the collimator matches rotation of the detector, e.g., orientation of the detector with respect to the collimator does not change. Consequently, when the operator rotates the detector, e.g., manually or with controls, the collimator is automatically rotationally repositioned.

Figure 4:
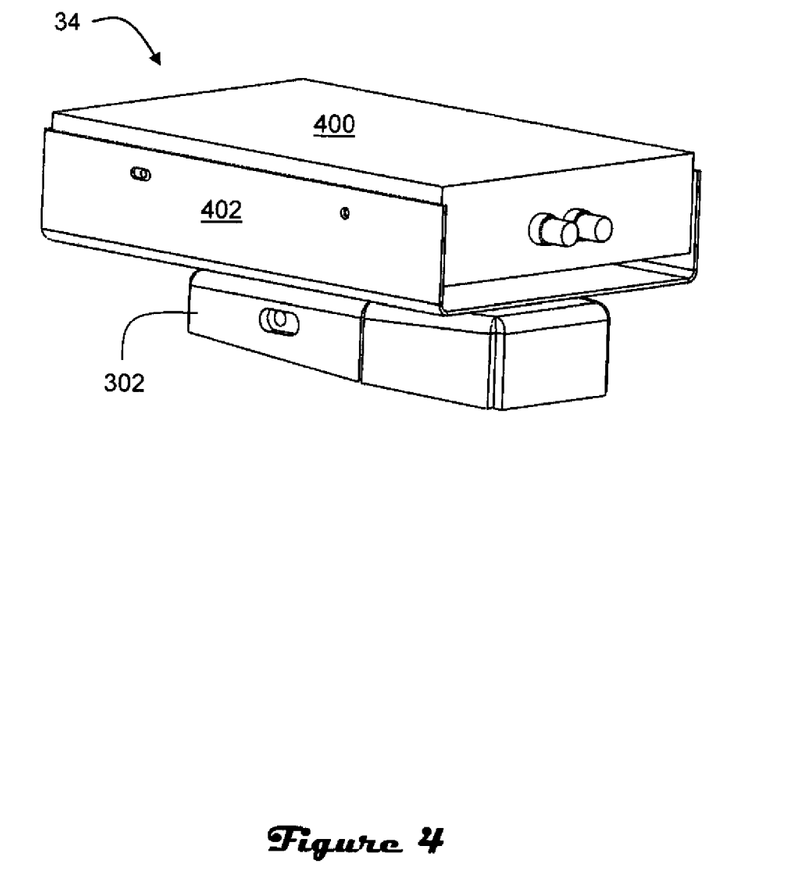
FIGS. 4, 5 and 6 illustrate the detector in greater detail.
Figure 5:
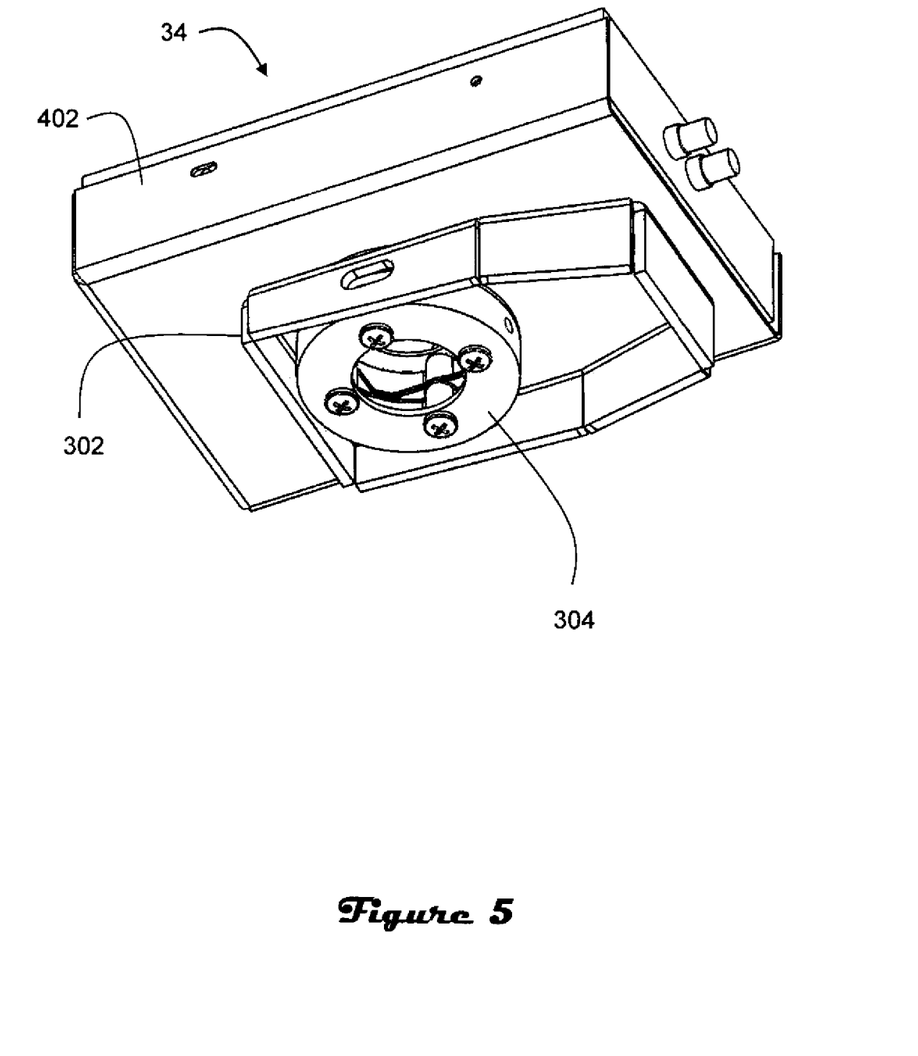
Figure 6:
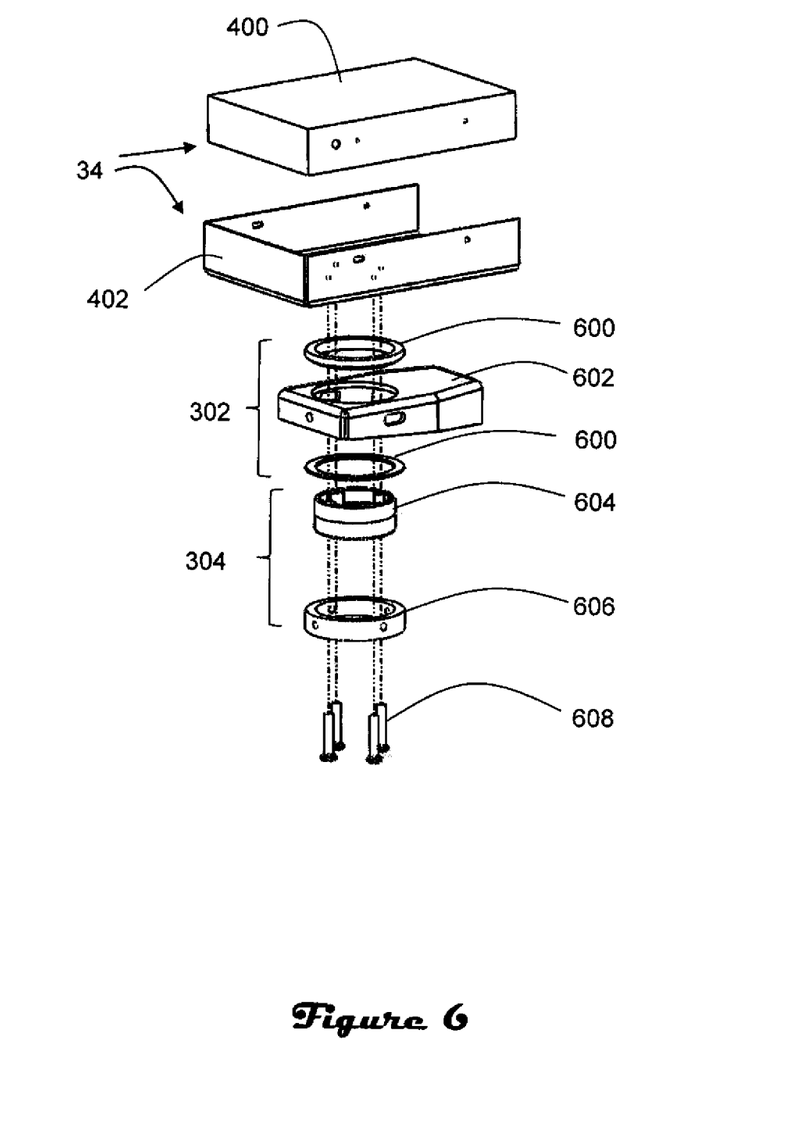

FIGS. 4 through 6 illustrate an embodiment of the detector 34 and associated rotation mechanism 302 and position sensor 304 in greater detail. The detector 34 includes a rectangular FPD 400 mounted in a chassis 402. The rotation mechanism 302 includes bearings 600 and a chassis 602. The position sensor 304 may include an encoder 604 and comparator 606. one of which is fixedly attached to the detector chassis 402, e.g., with fasteners 608, the other of which is fixedly attached to the rotation mechanism chassis. However, those skilled in the art will recognize that any of a variety of alternative position sensors which may have different principles of operation.

Figure 7:
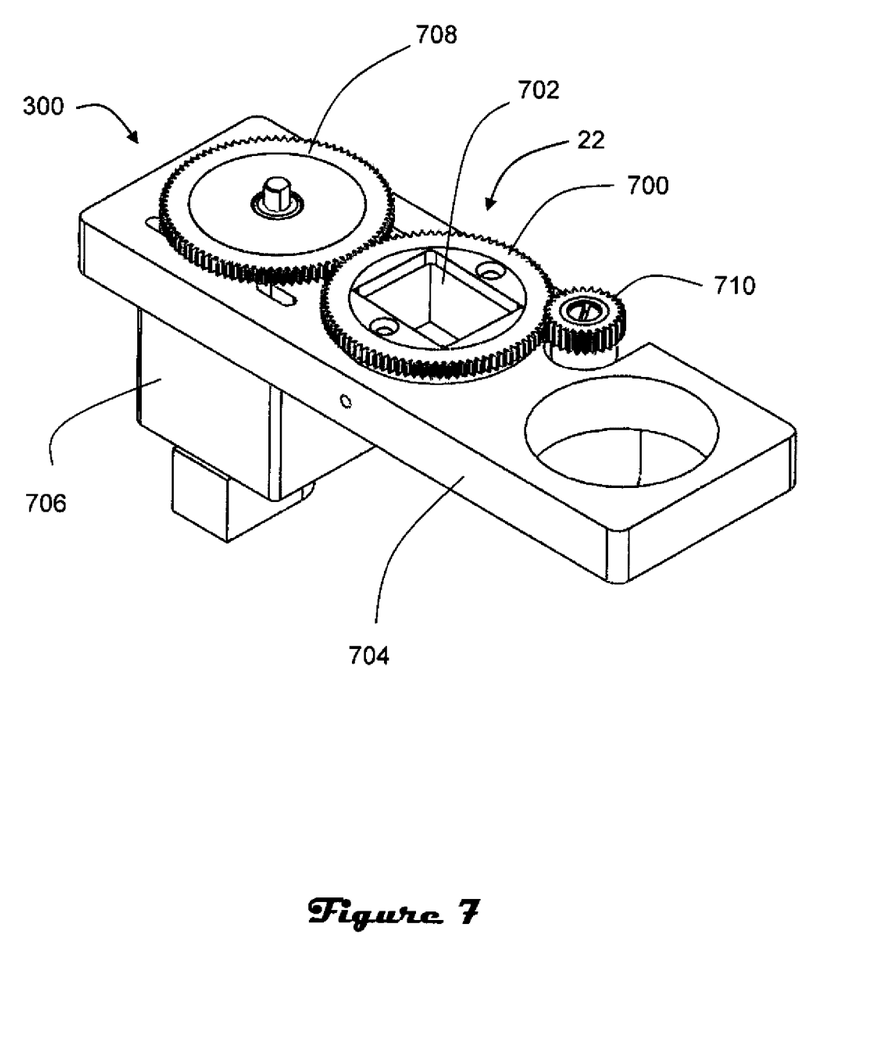
FIGS. 7 and 8 illustrate the collimator in greater detail.
Figure 8:
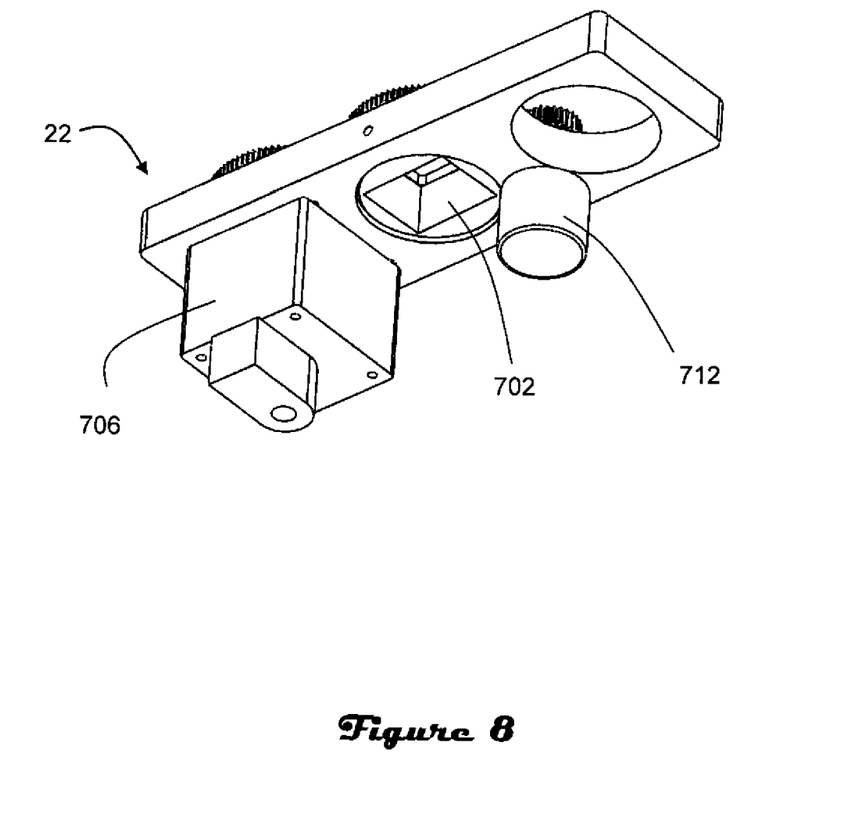

FIGS. 7 and 8 illustrate an embodiment of the collimator 22 and associated rotation mechanism 300 in greater detail. The collimator 22 includes a geared flange member 700 and a central portion 702 that defines a frustum-shaped opening. The central portion is disposed in an opening of a base plate 704 such that the collimator is rotationally movable relative to the base plate. A stepper motor 706 is mounted to the base plate and coupled to the collimator via a gear 708, the teeth of which engage the geared flange 700 of the collimator. The stepper motor 706 is coupled to the control system 306 (FIG. 3). More particularly, the stepper motor operates in response to input from the control system to cause the gear 708 to rotate, which in turn causes the collimator to rotate due to engagement with the teeth of the flange member 700. The magnitude and direction of the rotation are precisely controlled by the control system. Feedback may be provided to the control system via a geared member 710 which engages the geared flange portion 700. The geared member 710 may be coupled to a rotational position sensor 712.

At least the central portion 702 of the collimator 22 is constructed with a material that is opaque to x-rays. In one embodiment the collimator is a single molded piece (central portion and flange member) using a material that is impenetrable by x-rays but sufficiently non-malleable and abrasion resistant that it is also suitable for the gear teeth. For example, and without limitation, the collimator may be formed from a plastic such as a tungsten polymer material. However, the collimator may be an assembly with separate central portion and flange parts, e.g., a dense and more malleable metallic central portion and a less dense and less malleable metallic flange. Alternatively, the flange may be a multi-part assembly with the teeth formed from a material having particular characteristics.

Figure 9:
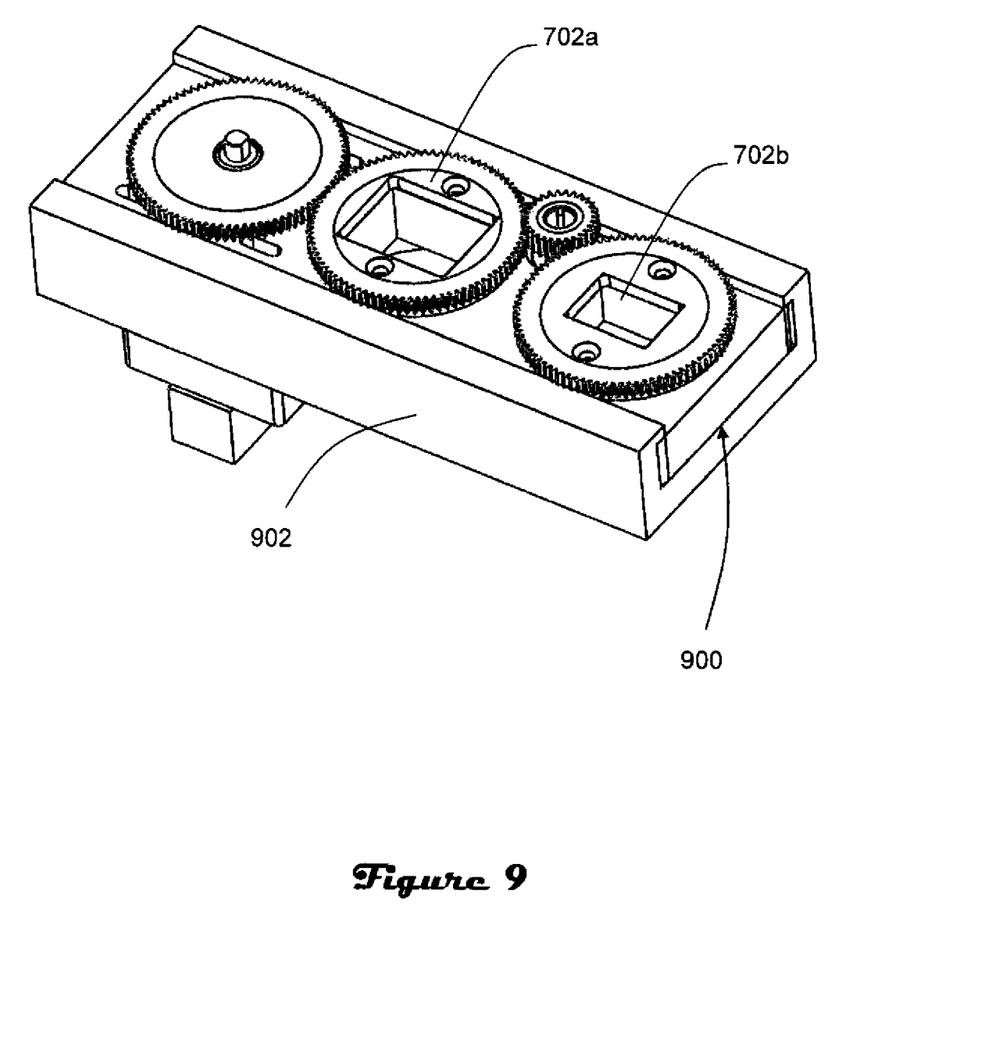
FIG. 9 illustrates an assembly for interchanging collimators.

FIG. 9 illustrates a mechanism for selectably interchanging collimators 702*a*, 702*b*. Two or more collimators are slidably mounted in series in a channel 900 of a base member 902. The collimators can be moved linearly in two directions, thereby enabling a selected collimator to be moved slidably into position relative to the detector 34 (FIG. 3). The collimators may be characterized by openings with various different shapes. Consequently, the operator can easily reconfigure the imaging system to utilize a collimator having an opening with a desired shape selected from a set of collimators mounted in the base without adding or removing a collimator from the system. One or more sensors indicate which collimator is in position for active use. Information from the sensor may be provided to computer processing 62 (FIG. 1) in order to facilitate image generation, processing and display. For example, the source field from source 20 (FIG. 3) may be adjusted in response to the collimator that is positioned for use.

Figure 10:
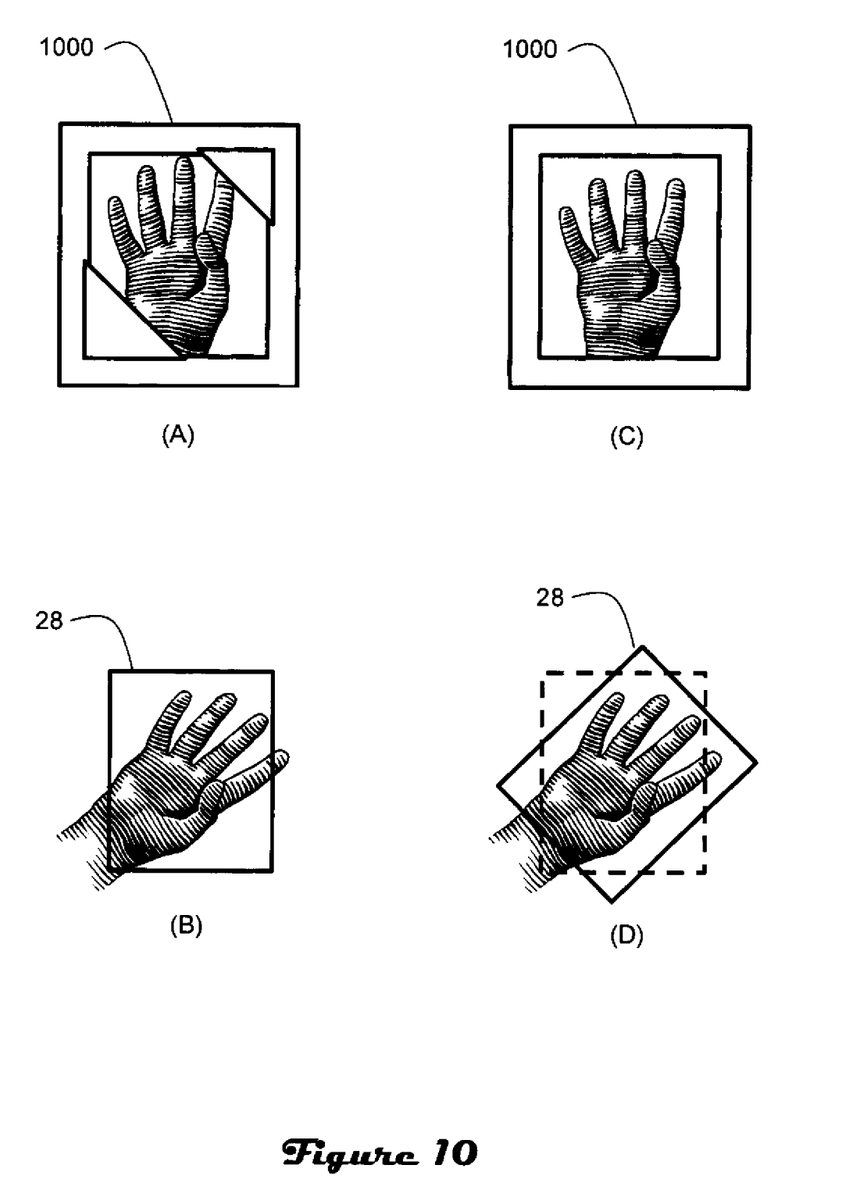
FIG. 10 illustrates operation of the user interface in greater detail.

FIG. 10 illustrates aspects of the computer processing 62 (FIG. 1) and user interface 68 (FIG. 1) in greater detail. The user interface includes a display 1000 for presenting an x-ray image to the operator. The computer processing controls presentation of the image on the display such that it is de-coupled from orientation of the target anatomy relative to the detector. Enabling the image to be displayed such that a particular orientation of the target anatomy as presented allows the operator to, for example, view an image of a hand such as in FIG. 10A with the fingers pointing upward on the screen regardless of how the hand is oriented relative to the detector in corresponding FIG. 10B. However, such orientation control is typically static once set, and in some cases a portion of the target that the operator wishes to view may not initially be within the field of the detector. In the illustrated example a fingertip and part of the wrist are not imaged in FIG. 10A because they are outside the field of view of the detector as shown in corresponding FIG. 10A. In order to move the portion of the target that is not being imaged into the field of view the target may be moved. Alternatively, or additionally, the detector can be rotated as described above. As shown in FIG. 10D the portions of the fingertip and wrist that were not imaged in FIG. 10B are imaged when the detector is rotated. However, the inventors have recognized that rotational movement of the detector and collimator could cause somewhat undesirable or disorienting changes to the displayed image, particularly if the detector is rotated during a medical procedure. In one embodiment the computer processing is coupled to the control system in order to monitor and react to rotational movement of the detector and collimator. For example, the computer processing may counter-rotate pixels of the image relative to the rotation of the detector such that the desired orientation of the target is not changed when the detector and collimator are rotated such as shown in FIG. 10C which corresponds to FIG. 10D. As a result, image orientation processing is dynamic, e.g., maintaining an image of a hand with fingertips pointed upward regardless of the position of the hand relative to the detector and also regardless of rotation of the detector.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system. may be embodied using a variety of specific structures. Accordingly, the invention should not be viewed as limited except by the scope and spirit of the appended claims.

What is claimed is:

1. A method of operating an X-ray imaging device having an X-ray source assembly including an X-ray source and a collimator, and a detector separated by a gap from the X-ray source, the method comprising:

receiving a signal from a position sensor associated with a position of the detector;
moving a position of the collimator relative to the X-ray source, based at least in part on the received signal; and
emitting an X-ray from the X-ray source to obtain an image of a patient's target anatomy.

2. The method of claim 1, wherein moving a position of the collimator relative to the X-ray source comprises manually moving the collimator relative to the X-ray source.

3. The method of claim 1, wherein moving a position of the collimator relative to the X-ray source comprises rotating the detector relative to the X-ray source.

4. The method of claim 1, further comprising:
presenting the image to an operator on a display; and
displaying the patient's target anatomy in a selected orientation regardless of an orientation of the patient's target anatomy relative to the detector, and regardless of the detector's position.

5. The method of claim 4, wherein displaying the patient's target anatomy comprises displaying the patient's target anatomy placed between the collimator and the detector in real-time.

6. The method of claim 5, further comprising a processor arranged and configured to de-couple the selected orientation of the patient's target anatomy relative to the detector, and wherein displaying the patient's target anatomy in a selected orientation regardless of orientation of the patient's target anatomy relative to the detector comprises:
dynamically adjusting the image of the patient's target anatomy displayed on the display to maintain an orientation of the image regardless of a position of the detector.

7. The method of claim 6, wherein the processor is arranged and configured to counter-rotate pixels of the image of the patient's target anatomy relative to the detector such that the orientation of the patient's target anatomy is not changed when the detector and collimator are moved.

8. The method of claim 1, wherein the X-ray imaging device further includes a C-arm support assembly, the collimator and detector being mounted on opposite ends of the C-arm support assembly in facing relation such that an emitted X-ray beam from the X-ray source impinges on an input end of the detector, the collimator and detector being rotationally movable independent of the C-arm support assembly.

9. The method of claim 8, wherein an axis of rotation of the detector matches an axis of rotation of the collimator.

10. The method of claim 9, further comprising automatically moving the detector from a position of non-alignment with the collimator to a position of alignment with the collimator to match an orientation of the collimator; and
automatically rotating the detector to match the orientation of the collimator.

11. The method of claim 1, wherein the X-ray imaging device further includes:
a first position sensor arranged and configured to determine a rotational position of the collimator;
a second position sensor arranged and configured to determine a rotational position of the detector; and
a control system arranged and configured to:
control a rotational position of the detector to mirror a rotational position of the collimator responsive to determining a change in the rotational position of the collimator.

12. The method of claim 11, further comprising a rotation mechanism coupled to the detector, the method further comprises:

automatically moving the detector via the rotation mechanism based on detecting a change in the rotational position of the collimator using the first and second position sensors.

13. The method of claim 12, wherein automatically moving the detector comprises:
   receiving an indication of detected rotation of the collimator; and
   prompting, via the control system, the rotation mechanism to rotate the detector so that rotation of the detector matches rotation of the collimator.

14. The method of claim 1, wherein the collimator includes a plurality of independent selectable collimators, the method further comprises:
   selecting a desired collimator from the plurality of independent selectable collimators; and
   slidably moving the selected collimator into a position for use.

15. The method of claim 1, wherein the collimator is positioned inside the X-ray source assembly and the X-ray source assembly is manually rotatable.

16. The method of claim 1, wherein the detector is a flat panel detector.

17. The method of claim 1, wherein moving the position of the collimator includes adjusting the shape of an aperture of the collimator.

18. A method of operating an X-ray imaging device having an X-ray source assembly including an X-ray source and a collimator mounted on a first end of a support assembly and a detector mounted on a second end of the support assembly, the method comprising:
   emitting X-ray beams from the X-ray source to project onto the detector, wherein the collimator is configured to shape the emitted X-ray beams;
   receiving, at a processor, a position signal associated with a position of the detector;
   adjusting the collimator within the X-ray source assembly from a first configuration to a second configuration, based at least in part on the received position signal.

19. The method of claim 18, wherein adjusting the collimator comprises manually moving the collimator from the first configuration to the second configuration.

20. The method of claim 18, wherein the X-ray imaging device further includes a C-arm support assembly, the X-ray source assembly and detector being mounted on opposite ends of the C-arm support assembly in facing relation such that the emitted X-ray beams from the X-ray source impinges on an input end of the detector, the collimator and detector being rotationally movable independent of the C-arm support assembly.

21. A method of operating an X-ray imaging device having an X-ray source assembly including an X-ray source and a collimator, the method comprising:
   receiving a signal from a position sensor associated with a position of a detector separated by a gap from the X-ray source;
   moving a position of the collimator relative to the X-ray source, based at least in part on the received signal; and
   emitting an X-ray from the X-ray source to obtain an image of a patient's target anatomy within the gap.

22. The method of claim 21, wherein the X-ray imaging device further includes a support assembly, the X-ray source assembly mounted on a first end of the support assembly and the detector mounted on a second end of the support assembly, the position of the collimator and the detector independent of the support assembly.

23. The method of claim 21, further comprising matching rotational orientation of the collimator with the detector.

* * * * *